United States Patent [19]
Lang et al.

[11] Patent Number: 5,314,332
[45] Date of Patent: May 24, 1994

[54] DENTAL ARTICULATOR

[75] Inventors: Hans W. Lang, Leutkirch; Alfred Straka, Isny, both of Fed. Rep. of Germany

[73] Assignee: Kaltenbach & Voigt GmbH & Co., Biberach an der Riss, Fed. Rep. of Germany

[21] Appl. No.: 41,820

[22] Filed: Apr. 1, 1993

[30] Foreign Application Priority Data

Apr. 2, 1992 [DE] Fed. Rep. of Germany ....... 4211021

[51] Int. Cl.$^5$ ............................................. A61C 11/00
[52] U.S. Cl. ......................................... 433/66; 433/57
[58] Field of Search ...................... 433/56, 57, 58, 59, 433/61, 66, 67

[56] References Cited

U.S. PATENT DOCUMENTS

| | | | |
|---|---|---|---|
| 1,451,892 | 4/1923 | Reimche | 433/66 |
| 3,897,632 | 8/1975 | Beu | 433/57 |
| 3,905,112 | 9/1975 | Swanson | 433/57 |
| 4,260,377 | 4/1981 | Hobo et al. | 433/58 |
| 4,305,708 | 12/1981 | Beu | 433/66 |
| 4,323,346 | 4/1982 | Beu | 433/58 |

FOREIGN PATENT DOCUMENTS 3050413  1/1983  Fed. Rep. of Germany .
3911067  10/1990  Fed. Rep. of Germany .

Primary Examiner—John J. Wilson
Attorney, Agent, or Firm—Scully, Scott, Murphy & Presser

[57] ABSTRACT

In a dental articulator having articulator arms which extend forwards in their working position, of which one is mounted in two swivel/sliding joints to pivot about a swivel axis extending at right angles to the vertical longitudinal centre plane, said joints being arranged on both sides of the vertical longitudinal centre plane as mirror-images and being each formed by an articular recess in an articular housing and a spherical head that engages through an opening in the articular recess, and the articular recess has a sagittal guide surface, a Bennett guide surface and a lateral guide surface, and associated with each swivel/sliding joint is a locking device with a locking element for locking the associated swivel/sliding joint in its O-position (final biting position), and the locking element can be adjusted between a locking position and a releasing position allowing sliding movements in the associated swivel/sliding joint, a form-locking connection is provided between the locking element and the spherical head for an attachment between the lower part and the upper part that is effective in the longitudinal direction of the swivel axis.

18 Claims, 7 Drawing Sheets

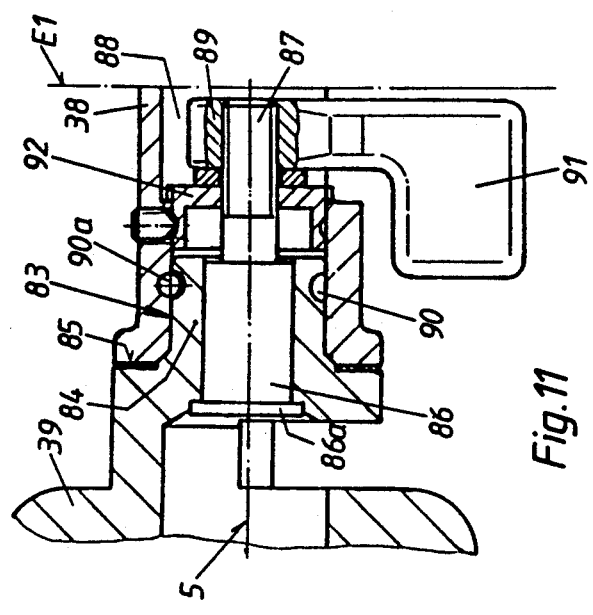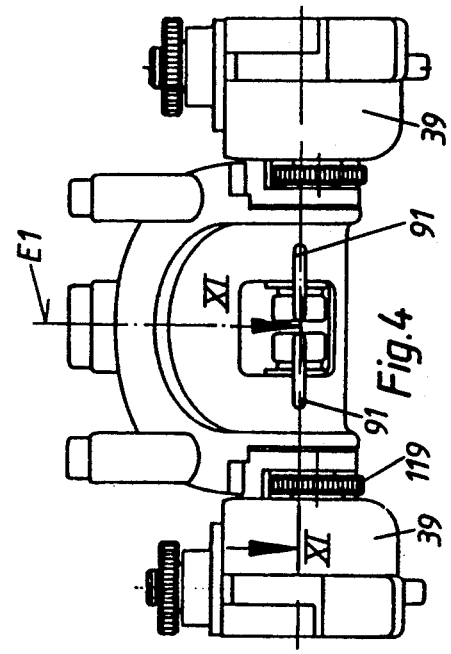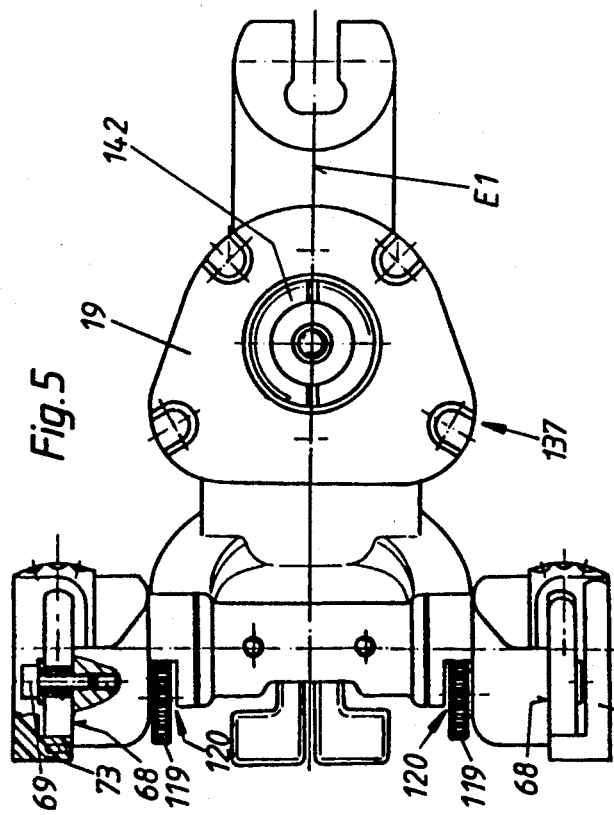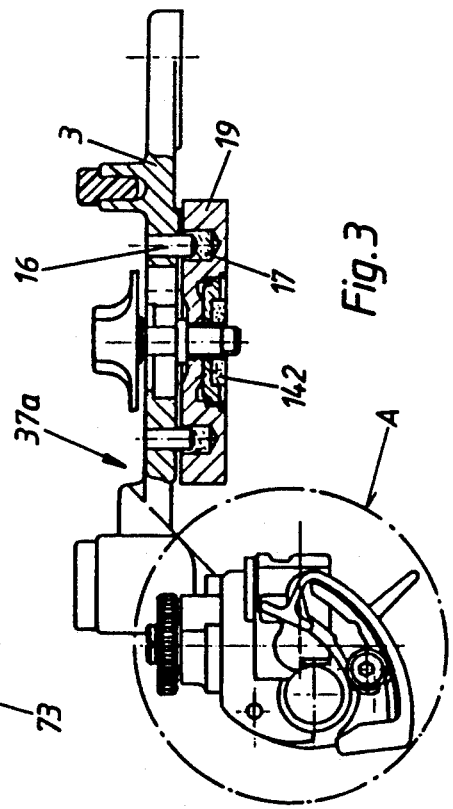

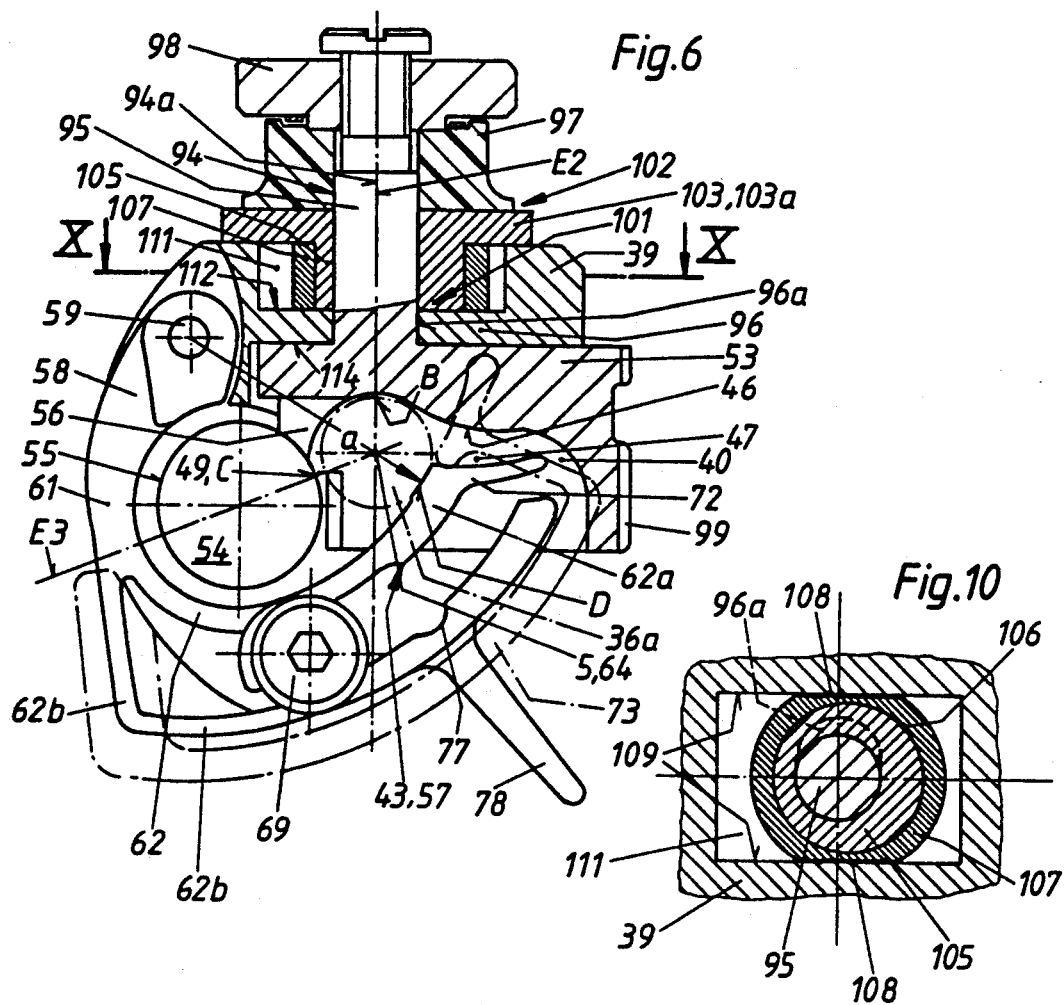
Fig.6
Fig.10
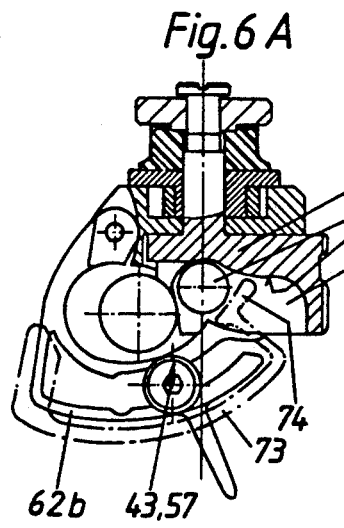
Fig.6A
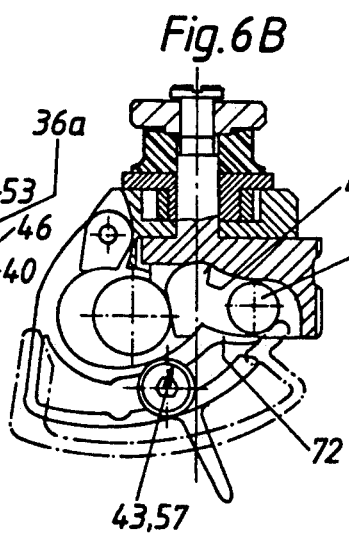
Fig.6B
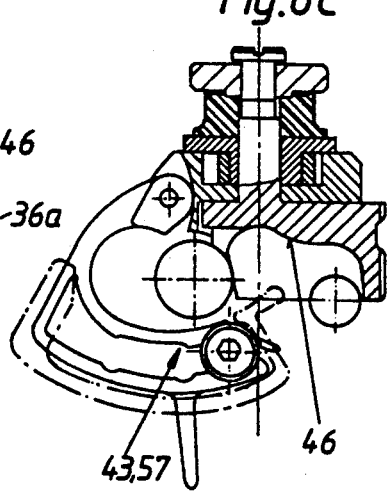
Fig.6C

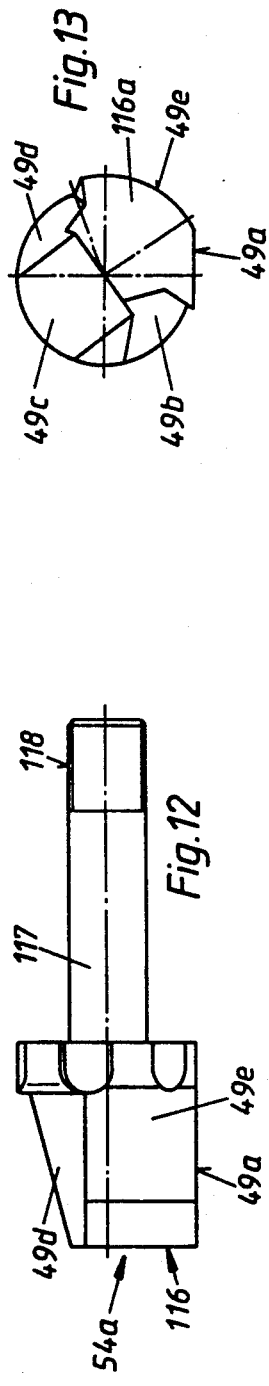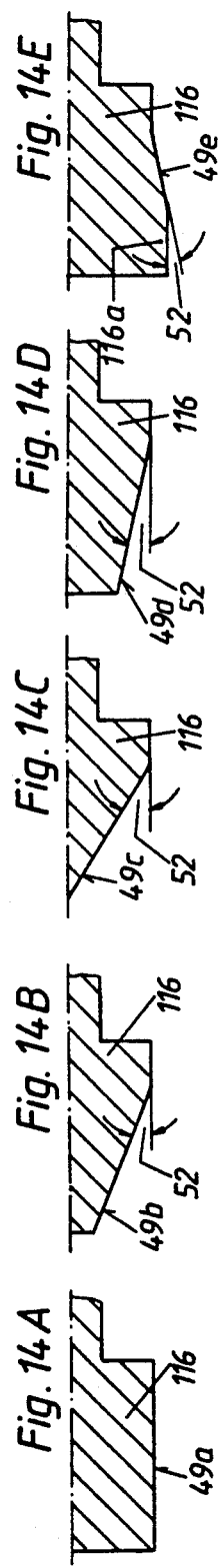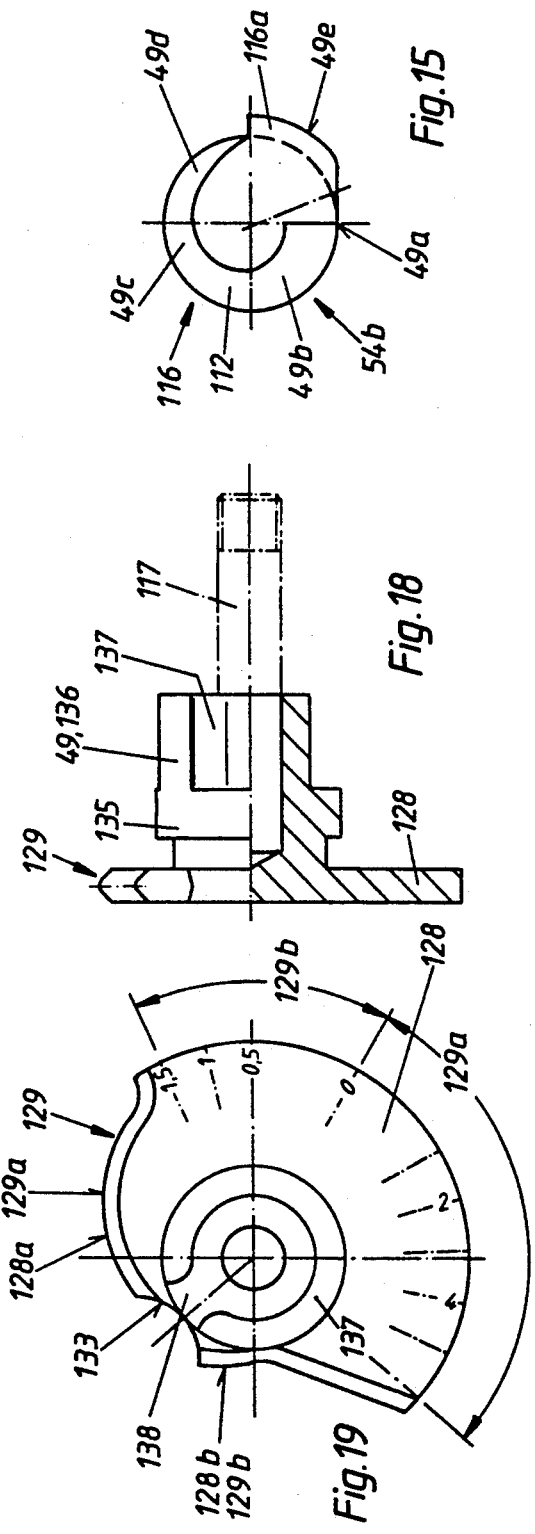

DENTAL ARTICULATOR

TECHNICAL FIELD OF THE INVENTION

The invention relates to a dental articulator.

BACKGROUND OF THE INVENTION AND PRIOR ART

A dental articulator is a movement simulator with which lower jaw movements can be simulated, which is necessary for the manufacture of tooth replacements, e.g. dentures or bridges.

The main parts of an articulator that are significant in this respect are the lower part and the upper part which carry the lower jaw tooth model and the upper jaw tooth model, and which are joined together in a rotating/sliding joint of which the axis of rotation in the final biting position extends at right angles to the vertical centre plane of the articulator. About this axis of rotation of the rotating/sliding joints, present on both sides in the articulator, the thus formed artificial set of teeth can be opened and closed by swivelling the upper part in the vertical centre plane. Furthermore, protrusive movements, laterotrusive movements and mediotrusive movements can be carried out, such as are made possible by the human jaw bone joint.

There are articulators in which the articular sphere is arranged on the lower part and the associated sliding joint guide is arranged on the upper part. An articulator of this kind is called an "arcon articulator". In contrast a non-arcon articulator is one in which the articular spheres are arranged on the upper part and the sliding joint guide is arranged on the lower part.

Known articulators are distinguished on the one hand between kinds which differ from one another with regard to their principle movement. With most articulators, the lower jaw movement is simulated by moving the upper part and thus the upper jaw.

In a known articulator the swivel/sliding joints are provided as articular heads directed upwards, which are arranged on upright supporting limbs of the articulator and engage in articular recesses open on the underside in articular housings arranged on the upper part. With this known configuration the spherical heads are held in the O-position by means of screws pushing against them.

A similar configuration is provided with another known articulator. In this known configuration the spherical heads are pushed by means of the screws obliquely inwards, at the same time against the lateral guide surface and the Bennett guide surface of the associated articular recess.

The two known configurations are disadvantageous for several reasons. One disadvantage is that the Bennett movement is restricted or at least does not correspond to the anatomical factors of the human body. On the other hand, due to the presence of the screws, very complicated operation is inevitable, e.g. when the articulator is to be adjusted or the upper part is to be dismounted from the lower part. Furthermore these known configurations are unsuitable for adjustable articular guide surfaces, e.g. the lateral guide surface or the Bennett guide surface. In both cases adjustments of the guide surfaces lead to positional differences between the lower part and the upper part.

OBJECT OF THE INVENTION

It is an object of the invention to improve the attachment between the lower and upper part and furthermore to provide a construction that is easy to assemble and disassemble and which enables the attachment to be effected in a user friendly manner.

SUMMARY OF THE INVENTION

According to the present invention there is provided a dental articulator having articulator arms which extend forwards in their working position, of which one is mounted in two swivel/sliding joints to pivot about a swivel axis extending at right angles to the vertical longitudinal centre plane, said joints being arranged on both sides of the vertical longitudinal centre plane as mirror-images and being each formed by an articular recess in an articular housing and a spherical head that engages through an opening in the articular recess, and the articular recess has a sagittal guide surface, a Bennett guide surface and a lateral guide surface, and associated with each swivel/sliding joint is a locking device with a locking element for locking the associated swivel/sliding joint in its O-position (final biting position), and the locking element can be adjusted between a locking position and a releasing position allowing sliding movements in the associated swivel/sliding joint, wherein a form-locking connection is provided between the locking element and the spherical head for an attachment between the lower part and the upper part that is effective in the longitudinal direction of the swivel axis.

In an embodiment according to this aspect of the invention, the mutual attachment between the upper part and the lower part is ensured by a form-locking connection which is effective in the locking position of the locking element between the latter and the associated spherical head. In the locking position, accurate attachment is ensured by this means, and by adjusting the locking element into its releasing position, the locking position is released automatically and the associated joint can carry out the desired sliding movement. In this aspect of the invention the O-position of the joint is independent of guide surfaces of the joint that extend transverse to the swivel axis. This independence also makes it possible to make the guide surfaces adjustable without impairing the attachment.

According to the present invention there is provided a dental articulator having articulator arms which extend forwards in their working position, of which one is mounted in two swivel/sliding joints to pivot about a swivel axis extending at right angles to the vertical longitudinal centre plane, said joints being arranged on both sides of the vertical longitudinal centre plane as mirror-images and being each formed by an articular recess in an articular housing and a spherical head that engages through an opening in the articular recess, and the articular recess has a sagittal guide surface, a Bennett guide surface and a lateral guide surface, and associated with each swivel/sliding joint is a locking device with a locking element for locking the associated swivel/sliding joint in its O-position (final biting position), and the locking element can be adjusted between a locking position and a releasing position allowing sliding movements in the associated swivel/sliding joint, wherein in the locking position the locking element urges the associated joint into its O-position and pushes elastically against the spherical head with a force that is preferably directed to the rear, obliquely upwards and at right angles to the swivel axis.

With an embodiment of this aspect of the invention an accurate O-position of the joint is achieved with simple design, because only the part of the joint against which the articular head is to be urged elastically needs to be available. The other part of the joint is formed by the elastic, resiliently effective locking element.

According to the present invention there is provided a dental articulator having articulator arms which extend forwards in their working position, of which one is mounted in two swivel/sliding joints to pivot about a swivel axis extending at right angles to the vertical longitudinal centre plane, said joints being arranged on both sides of the vertical longitudinal centre plane as mirror-images and being each formed by an articular recess in an articular housing and a spherical head that engages through an opening in the articular recess, and the articular recess has a sagittal guide surface, a Bennett guide surface and a lateral guide surface, and associated with each swivel/sliding joint is a locking device with a locking element for locking the associated swivel/sliding joint in its O-position (final biting position), and the locking element can be adjusted between a locking position and a releasing position allowing sliding movements in the associated swivel/sliding joint, wherein a resilient part is effective between the lower part and the upper part which, in the releasing position of the locking element, urges the swivel/sliding joint into its O-position and/or holds the sagittal guide surface and the spherical head in sliding contact.

By means of an embodiment of this aspect of the invention operation when effecting sliding movements in the joints is facilitated because the user can carry out the movements without having to pay attention to whether there is a contact between the spherical head and the respective guide surface in use. This may be the sagittal guide surface, the Bennett guide surface and/or the lateral guide surface. Within the scope of the invention it is possible that the elastic spring force only acts upwards against the sagittal guide surface. This spring force is preferably aimed so that automatic abutment of the spherical head against the sagittal guide surface is ensured and furthermore the joint is automatically returned to its O-position.

According to the present invention there is provided a dental articulator having articulator arms which extend forwards in their working position, of which one is mounted in two swivel/sliding joints to pivot about a swivel axis extending at right angles to the vertical longitudinal centre plane, said joints being arranged on both sides of the vertical longitudinal centre plane as mirror-images and being each formed by an articular recess in an articular housing and a spherical head that engages through an opening in the articular recess, and the articular recess has a sagittal guide surface, a Bennett guide surface and a lateral guide surface, and associated with each swivel/sliding joint is a locking device with a locking element for locking the associated swivel/sliding joint in its O-position (final biting position), and the locking element can be adjusted between a locking position and a releasing position allowing sliding movements in the associated swivel/sliding joint, wherein the locking element is preferably adjustable beyond its releasing position into an open position vacating the opening of the articular recess.

An embodiment of this aspect of the invention enables user-friendly adjustment of the locking element between its locking position and its open position, as a result of which it is easy to dismount or attach the upper part.

Embodiments of aspects of the invention may include features which lead to simple, easily adjustable, operationally reliable types of construction that can be manufactured economically. Various embodiments relate to optional adjustment of more varied guide surfaces of the swivel/sliding joints.

BRIEF DESCRIPTION OF THE DRAWINGS

The invention and further advantages attainable thereby will now be described in more detail with reference to preferred exemplary embodiments and drawings, in which:

FIG. 3 shows an upper part of the articulator in side elevation from the left, partly sectioned;

FIG. 4 shows the upper part in back elevation;

FIG. 5 shows the upper part in lower elevation;

FIG. 6 shows the detail indicated in FIG. 3 by A in an enlarged representation, partly sectioned;

FIGS. 6A to 6C show the detail A in different functional positions of a joint-lock bow of the articulator;

FIG. 10 shows the partial section X—X in FIG. 6;

FIG. 11 shows the partial section XI—XI in FIG. 4 in an enlarged representation;

FIG. 12 shows a modified lateral guide part in front elevation;

FIG. 13 shows the lateral guide part in side elevation from the left;

FIGS. 14A–14E show lateral guide surfaces of the lateral guide part shown in FIG. 12;

FIG. 15 shows a lateral guide part in a further modified embodiment in side elevation;

FIG. 18 shows a protrusion guide part in front elevation;

FIG. 19 shows the guide part in side elevation from the right;

DETAILED DESCRIPTION OF PREFERRED EMBODIMENTS ACCORDING TO THE INVENTION

Figure 1:
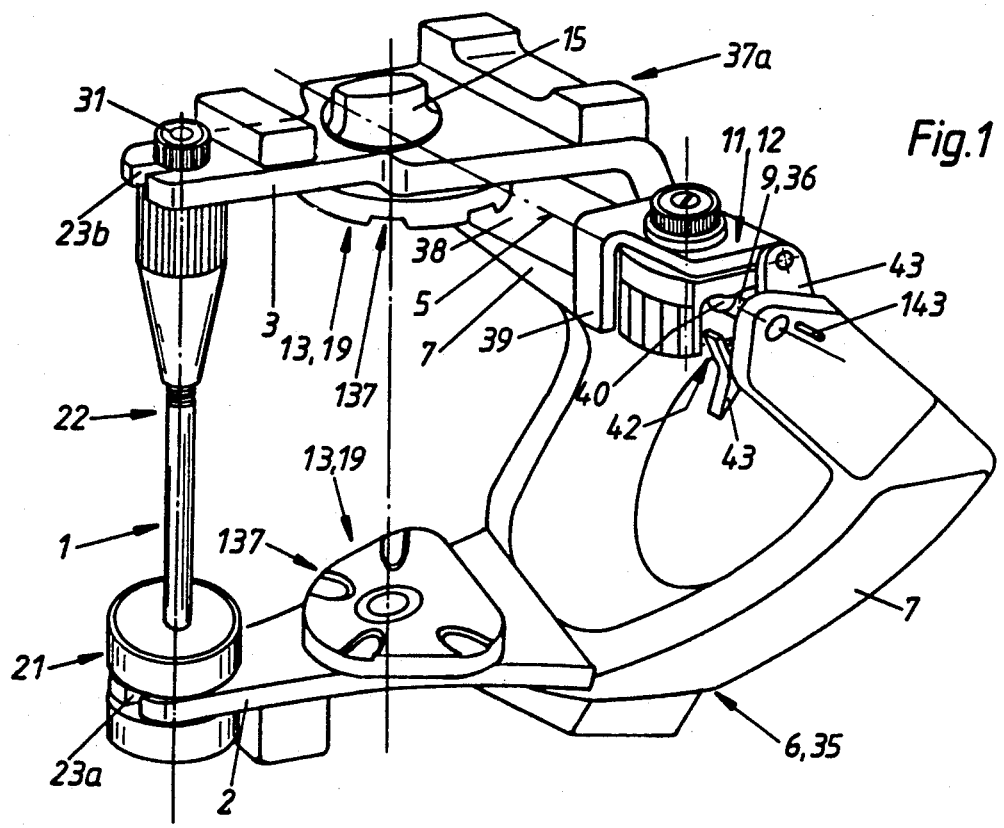
FIG. 1 shows an articulator according to the invention in a perspective front/side elevation.

Only the main parts of the articulator 1 that are operationally significant in the present context will be described below. These are a lower articulator arm 2 and an upper articulator arm 3 of which the latter is mounted pivotably to a U-shaped mount or frame 6 having two lateral, upwardly extending frame limbs 7, to pivot about a swivel axis 5 extending at right angles to a vertical longitudinal centre plane El of the articulator extending from the front to the rear. The swivel bearing parts 9 to the sides of the frame are arranged at the upper ends of the frame limbs 7. It is preferably a so-called arcon articulator with rotatory or swivel/sliding joints 11 of which the sliding guide 12 is located on the upper articulator arm 3. Provided in the rear or middle regions of the articulator arms 2, 3 on their facing sides are respective placement areas 13 for associated tooth models or tooth model base parts which can each be positioned and fastened by a screw 15 passing through the articulator arm 2, 3 in a through hole and by alignment pins 16 projecting from the articulator arms 2, 3. In the Figures two primary bases 19 for a lower jaw and an upper jaw tooth model UK, OK are shown. Mounted at the front end of the one articulator arm 2, 3, here the lower articulator arm 2, is an incisal table 21 on which an upwardly extending, telescopic supporting pin 22 is supported detachably with its free end, and which is detachably attached to the end of the other articulator arm, here the upper articulator arm 3. The fastening or securing elements for the incisal table and the supporting pin 22 are preferably the same or match one another so that the incisal table 21 and the supporting pin 22 can be secured, in positions opposite one another, as desired either on the upper or the lower articulator arm 2, 3. In each case, a respective fitting slit 23a, 23b serves for mounting purposes, preferably extending in the longitudinal centre plane and passing vertically through the associated articulator arm 2, 3 and opening at its free end. In these similar fitting slits the incisal table 21 or supporting pin 22, as desired, can be mounted through correspondingly fitting waists up to mutually coinciding slit ends which form stops limiting the sliding-in movement, and can be screwed to the associated articulator arm 2, 3 by a screw part 31. The two primary bases 19 have alignment holes 17 for the alignment pins 16 (FIG. 3).

The articulator 1 comprises a lower part 35 which includes the lower articulator arm 2, the frame 6 and articular heads 36 projecting coaxially inwards from the insides of the frame limbs 7, and an adjustable upper part 37a which includes the upper articulator arm 3, an articular hub part 38 and two articular housings 39 attached laterally thereto in which the articular heads 36 are mounted in respective swivel/sliding joints 11. The upper part 37a is held detachably in the swivel/sliding joints 11 by means of two centric locks 42 associated with the articular housings 39. Each centric lock 42 has a C-shaped locking bow 43 which, in its retracted closed position, reaches under the associated articular head 36 and hereby secures it in the existing lateral articular recess 40 that is open downwards.

Figure 2:
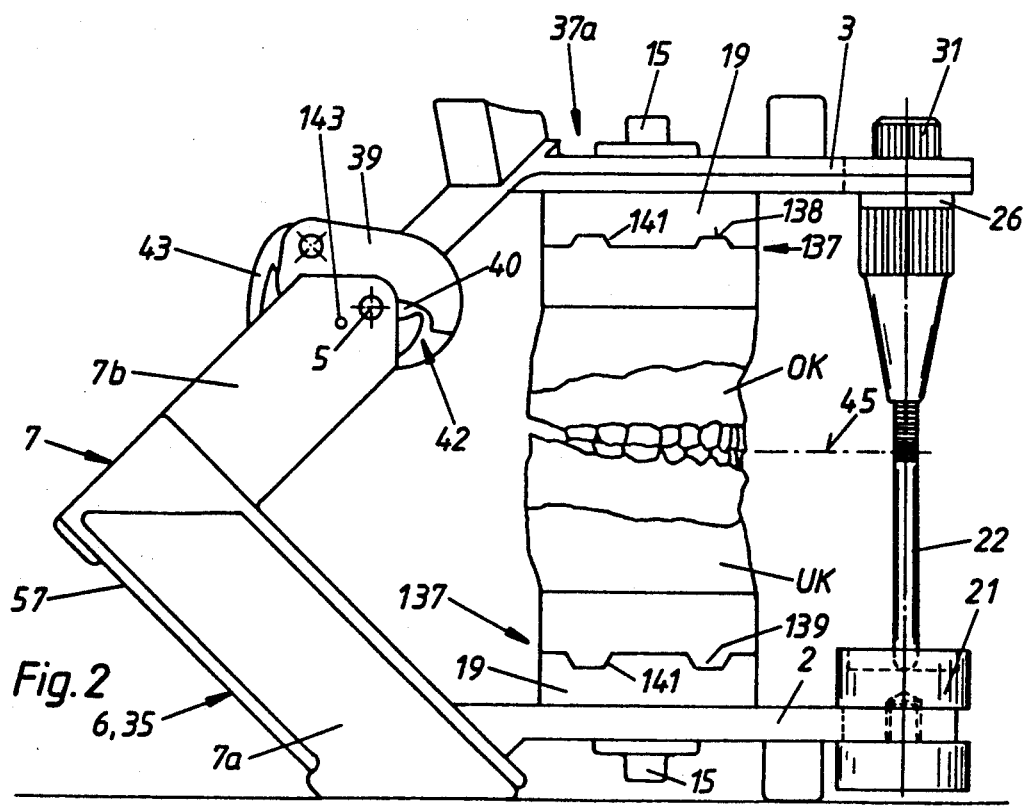
FIG. 2 shows the articulator in side elevation from the left.

The articulator arms in the present exemplary embodiments are preferably arranged so that not only the lower articulator arm 2 but preferably also the upper articulator arm 3 is arranged substantially horizontally when the lower jaw UK and the upper jaw OK lie one on the other (FIG. 2) in the final biting position. The occlusion plane 45 also extends substantially horizontally and thus parallel to the horizontal table or working surface carrying the articulator 1.

From this final biting position, lower jaw movements can be simulated in the articulator 1 which correspond to the anatomical conditions of the human body. However, in the present exemplary embodiment, for this purpose it is not the lower jaw UK or the lower part 35 which can be moved; rather it is the upper part 37 with the upper jaw OK which can be moved relative to the lower part 35 (arcon articulator). Hereby the movements mainly involved are opening and closing movements, protrusive movements, laterotrusive movements and mediotrusive movements. To enable this, the lateral and downwardly open joints 11 or articular recesses 40, arranged as mirror-images of one another with reference to the vertical longitudinal centre plane El of the articulator 1, each have an upper sagittal guide surface 46 which inclines forwards in a curve, a Bennett guide surface 47 which, with the vertical longitudinal centre plane E1 of the articulator 1, forms an acute Bennett angle 48 that is open at the front, and an upright lateral guide surface 49, extending transverse to the vertical centre plane E1, which in the exemplary embodiment shown in FIGS. 3 to 9 extends parallel to the swivel axis 5 in the final biting position, namely the O-position, but can also form a so-called shift angle 52 (indicated in FIG. 9) with the horizontal swivel axis 5. The articular recesses 40 are thus bounded rearwardly by the respective associated lateral guide surface 49, inwardly by the Bennett guide surface 47 and upwardly by the sagittal guide surface 46. The latter curves forwards and is first curved in a convex manner and then in a concave manner so that its front end region extends in a downward arc.

Each articular recess 40 is arranged in an associated bearing part 53 that is preferably adjustable in four degrees of freedom and can be fixed in the respective disposition and mounted in the associated articular housing 39, which will be described below.

In the present embodiment the lateral guide surface 49 is not part of the associated bearing part 53 but a separate component likewise mounted on the associated articular housing 39 which, in the present embodiment, is formed by a cylinder 54 which is mounted so that it is offset so far to the rear and below and parallel with the swivel axis 5, which in the O-position is the centre axis of the articular heads 36, so that its outer surface 55 forms the lateral guide surface 49. The arrangement of the cylinder 54 is such that in the O-position its outer surface 55 together with the rear end region of the sagittal guide surface 46 bounds rearwardly the articular pins 36 formed by a respective spherical head 36a. In this rear bearing position, which corresponds to the final biting position, the contact point B between the spherical head 36a and the sagittal guide surface 46 lies in a vertical transverse plane E2 containing the swivel axis 5, while the contact point C between the spherical head 36a and the lateral guide part 54 lies in a plane E3 containing the swivel axis 5 that may be arranged approximately horizontally, preferably inclined to the rear at an angle of about 30°. To the rear of the contact points B and C the associated articular recess 40 may be open or can have a space or slit 56 which can extend from the contact point B in the shape of a crescent moon and which enables retroversive movement of the upper part 37a of, e.g., up to about 1.5 mm when the lateral guide part 54 is dismounted, which will be described below.

Each of the two centric locks 40, arranged as mirror-images of one another with reference to the vertical longitudinal centre plane E1, has a joint locking part 57 that can be adjusted between a locking position as shown in FIG. 6, a sliding joint releasing position as shown in FIG. 6A and 6B, and an open position as shown in FIG. 6C, and can be fixed releasably in the respective position. In the present embodiment the securing part 57 is formed by the crescent shaped locking bow 43 that is mounted on an articular bolt to pivot with its foot end 58 in the rear upper region of the associated articular housing 39 about a joint axis 59 extending parallel to the swivel axis 5, whereby starting from the foot end 58 it extends first with a rear bow part 61 first downwards and them forwards with a lower bow part 62 in the form of a hook, whereby the latter reaches under the lateral guide part 54 and the associated spherical head 36a at a distance and thereby, in its locking position shown in FIG. 6, projects with its free end into the associated articular recess 40.

Figure 9:
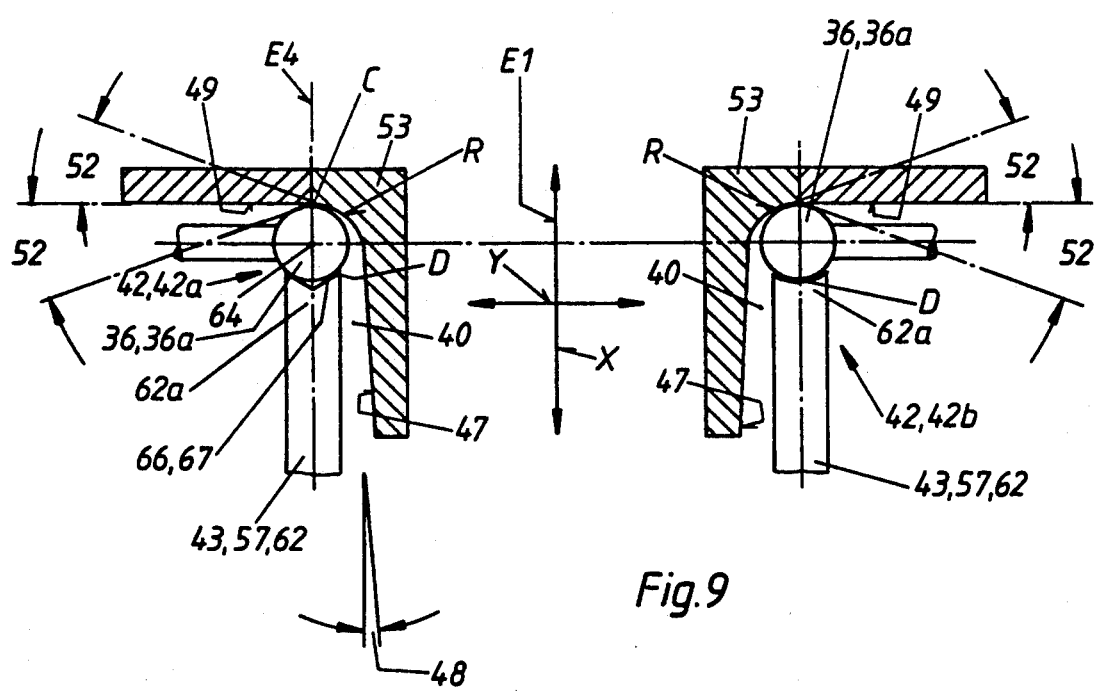
FIG. 9 shows a horizontal section through the joint of the articulator viewed from above.

The locking bow 43 is arranged and mounted pivotably in a vertical plane E4 extending parallel to the vertical longitudinal centre plane E1 which, in the normal centre position of the upper part 37 includes the centre point 64 of the spherical head 36a (see FIG. 9). The locking bow 43 consists of hard, elastic material, e.g. hard steel or spring steel. In its normal position the free end region 62a of the lower bow part 62 is at a radial distance from the swivel axis 59 that is a little smaller than the amount a between the swivel axis 59 and the outer surface 55 of the lateral guide part 54 facing away therefrom. Consequently, when pivoting the locking bow 43 into the locking position shown in FIG. 6, the free end region 62a of the lower bow part 62 is bent slightly, radially outwards so that in the contact point D between it and the spherical head 36a it pushes in a radially inward direction and thus pulls the upper part into the contact points B, C against the spherical head 36a. The upper part 37a is hereby in the vertical plane E4, i.e. it is centered and securely mounted in the longitudinal direction X in the sense of a three-point bearing.

One of the two centric locks 42, here the centric lock 42a arranged on the left in FIG. 9, is formed as an effective fixed bearing in the locking position of the locking bow 43 with reference to the longitudinal direction of the swivel axis 5 of the sliding joint 11, namely the transverse direction Y, while the other, here the right centric lock 42b, is formed as a movable bearing. This is ensured by a form-locking connection integrated in the fixed bearing 42a which, in the O-position, prevents relative displacement between the lower and upper part 35, 37a in the longitudinal direction of the swivel axis 5, part 37a to pivot about the swivel axis 5. As is clearly shown in FIG. 9, this form-locking connection is formed by a groove 66 in the free end region 62a of the lower bow part 62 which groove extends in the vertical plane E4 and against whose groove flanks 67, which are preferably wedge-shaped, the spherical head 36a bears and thus the locking bow 43 together with the upper part 37a is centered in the transverse direction Y on the spherical head 36a. In the region of the movable bearing 42b the associated locking bow 43 is on the other hand not fixed in the longitudinal direction of the swivel axis 5. Here the bearing surface of the free end region 62a bearing against the spherical head 36a is a flat transverse surface or it can also be rounded in a concave manner with a radius that is larger than the radius of the spherical head 36a, as shown in FIG. 9.

The aforementioned centering of the upper part 37a relative to the lower part 35 in the transverse direction Y enables the radii of curvature R (FIG. 9) between the Bennett guide surface 47 and the lateral guide surface 49 in the guiding recess 40 to be slightly larger than the radius of the associated spherical head 36a. A small crescent shaped space is hereby made on the inside of the spherical heads 36a. This embodiment enables, in the case of a mediotrusion movement, a so-called initial bend at the start of a Bennett movement.

The two locking bows 43 each lie with their inner sides against a bearing surface 68 (FIG. 5) of the associated articular housing 39 that is directed outwards laterally, through which lateral centering of the upper part 35 is ensured. In addition the locking bows 43 are stabilised at a radial distance from the swivel axis 59 in the vertical plane E4. For this purpose a stabilising part is provided along which the lower bow part 62 slides on its swivel path. In the present exemplary embodiment the stabilising part is formed by a stabilising screw 69 which is screwed on the outside from the lower bow part 62 into the respective associated articular housing 39 and with its screw head forms on the inside and/or on the outside lateral guide surfaces for the lower bow part 62 and thus stabilises it laterally.

A bow extension 72 is arranged, bent radially, obliquely outwards from the free end 62a of the lower bow part 62, so that in the sliding joint releasing position shown in FIG. 6A and 6B it extends more or less parallel to the sagittal guide surface 46. The arrangement is such that, in this sliding joint releasing position, in which the upper part 37a can be displaced relative to the lower part 35 along the sagittal guidance (see in particular FIG. 6B), the bow extension 72 pushes upwards against the spherical head 36a. Hereby the abutment of the sagittal guide surfaces 46 against the associated spherical heads 36a is ensured not only in the O-position of the swivel joint 11 but also in its optional sliding position. The intended lower jaw movements can thus be carried through anatomically without the user having to assist manually to ensure the abutment against the sagittal guide surface 46 as is the case in known configurations. The user can thus direct his attention and efforts during a displacement more to the conditions in the region of the teeth.

The bow extension 72 can also fulfill the function of preventing dismounting of the upper part 37a from the lower part 35 in the sliding joint releasing position shown in FIGS. 6A and 6B. This is achieved in that the bow extension 72 closes the underside opening of the articular recess 40 to such an extent that the associated spherical head 36a cannot come out (see FIG. 6B).

The afore-mentioned elastic contact pressure force and securement against dismounting may also be ensured by a spring-resilient add-on piece of the locking bow 43. Such a resilient part is indicated in outline in FIGS. 6–6C and shown to an enlarged scale in FIGS. 7 and 8 and indicated by 73. It has a flexible tongue 71 projecting over the free end of the lower bow limb 62 which pushes with an elastic spring force in the direction of the swivel axis 5 against the spherical head 36a.

Thus not only is the sagittal guide surface 46 prebiassed downwards against the spherical head 36a, but the articular housing 39 is also pulled obliquely downwards, namely into the O-position of the joint 11. Guidance of the upper part 37a is hereby substantially facilitated because the joint arrangement automatically returns to the O-position due to the spring forces. This return movement is at least assisted.

The guiding or stabilising screw 69 in the present exemplary embodiment also fulfils the purpose of fixing the associated locking bow 43 in its sliding joint releasing position (FIGS. 6A, 6B) in a manner which can be overcome elastically by exerting sufficient pressure, and of bounding the swivel movement in the closing position (FIG. 6) or open position (FIG. 6c). For this purpose depressions can be provided in the bow part 62 into which the shaft of the stabilising screw 69 can engage elastically due to the elasticity of the bow part 62. A second lower bow part 62b is preferably arranged, at a radially, outwardly directed distance, on the lower bow part 62, which second bow part is curved approximately parallel to the first bow part 62 and is joined at its rear end, preferably in one piece, to the locking bow 43, here at the lower bow part 61. In this embodiment a locking recess 77 is preferably provided in the inside of the second, lower, elastically outwardly bendable bow part 62b for engagement, which can be overcome with the exertion of sufficient force, with the shaft of the stabilising screw 69 in the sliding joint releasing position. Further locking recesses 77 of this kind or also stops bounding the path of movement between the bow parts 62, 62b can be provided for the open position and/or locking position of the locking bow 43. Formed on the outside or underside of the second bow part 62b is a rod-shaped handle part 78 extending radially outwards which can be grasped manually to pivot the locking bow 43 to its desired position.

Figure 7:
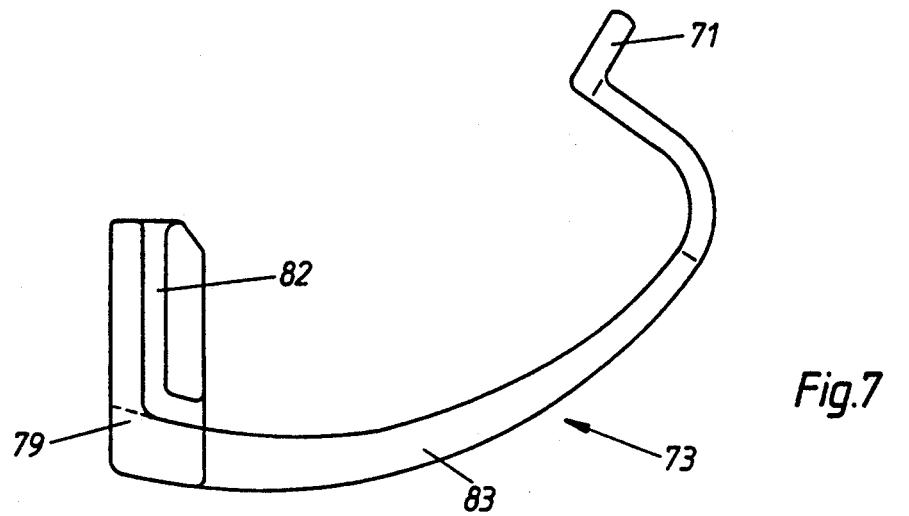
FIG. 7 shows a resilient element that can be mounted to the lock bow, in side elevation from the left and in an enlarged representation.
Figure 8:
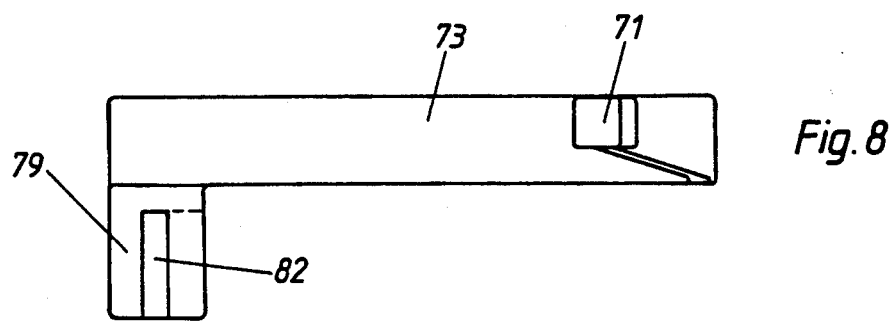
FIG. 8 shows the resilient element in plan view.

As is clearly shown in FIG. 7 the resilient part 73 comprises a rectangular block-shaped foot piece 79 from the lower end of which a resilient part bow 83 extends forwards and upwards in an arc shape which, at its free end carries the resilient tongue 71 which extends forwards obliquely upwards. As shown in FIG. 8 the resilient part bow 83 and the resilient tongue 71 are offset outwardly relative to the foot piece 79. Formed in the foot piece 79 is a vertical, inwardly open guide slit 82 with which the foot piece 79 can be mounted from outside on to an upright extending foot section 62b of the lower bow part 62b and can be held in a form-locking manner between the bow parts 62, 62b. When viewed from above the resilient part bow 83 and the resilient tongue 71 are located on the outside next to the associated locking bow 43, whereby the resilient tongues 71 of both resilient parts 73 push against the tapered articular head shaft 36b of the associated articular head 36. The resilient parts 73 formed and arranged as mirror images with reference to the vertical longitudinal centre plane E1 are preferably injection molded parts of an elastic plastics material.

The afore-mentioned three degrees of freedom for the bearing part 53 of each swivel/sliding bearing 11 will be described below.

The first degree of freedom includes a pivot bearing 83 (FIG. 11) in which the associated articular housing 39 can be rotated about the swivel axis 5 and fixed in the relevant rotational position. Consequently the inclination of the sagittal guiding path 46 (which is also known in the art as a condyle path) can be adjusted as desired in an angle range between about −15° and +75° to the Frankfurt horizontals. To facilitate the adjustment a scale is mounted in the region of each joint between the associated articular housing 39 and the hub part 38 of the upper part 37a on the edge of the hub part 38 or of the articular housing 39. Preferably there are two scales, of which the one indicates the rotational position relative to the Kamper's plane and the other to the Frankfurt horizontals. The two pivot bearings 83 are arranged as mirror images with reference to the vertical longitudinal centre plane E1.

In the present embodiment each articular housing 39 has a circular bearing pin 84 projecting coaxially inwards, that is mounted to rotate with little play in a coaxial bearing bore in the hub part 38. By means of an abutment of the articular housing 39 with a ring shoulder surface 85 against the lateral front face of the hub part 38 the lateral exact position of the associated bearing housing 39 is ensured. Mounted coaxially to rotate in the bearing pin 84 is a cylindrical holding bolt 86 and projecting coaxially inwardly therefrom is a threaded shaft 87 which projects into a recess 88 that is arranged centrally in the hub part 38 and is open to the rear. Screwed onto each threaded shaft 87 of the holding bolt 86 is an adjusting nut 89 with a radial chuck lever 91, with which nut the holding bolt 86, that is preferably longitudinally displaceable but not rotatable in a radial wall 92, e.g. a fixed inserted extension piece, can be tensioned inwardly whereby it tensions with a bolt head 86a the associated articular housing 39 against the existing axial abutment and thus secures it against unintentional rotation. With the rotational positioning of the articular housing 39, the associated bearing parts 53 are positioned with reference to the inclination of their sagittal guide surface 46.

For additional axial securement of the rotatable articular housing 39 in the bearing hub 38 a peripheral groove 90 can be provided in the outer surface of the bearing pin 84 into which an engagement member attached to the bearing hub engages with little play. The latter is preferably formed by a pin 90a sitting in a secantal hole and which engages in the semi-circular peripheral groove 90 and thus prevents axial displacement whilst ensuring rotation.

The second degree of freedom is formed by a pivot bearing 94 (FIG. 6) in which each bearing part 53 can be rotated about a vertical axis of rotation 94a and can be fixed in the relevant rotational position. By this means a selected Bennett angle 48 from, e.g. about 5° to 25° can be set. The vertical axes of rotation 94a intersect the swivel axis 5, i.e. the bearing parts 53 can be adjusted horizontally about the O-point of the swivel/sliding bearing 11. In the present embodiment each bearing part 53 has a vertical, upwardly projecting bearing bolt 95 which passes upwards through and projects from a hole 96a through the wall 96 of the associated articular housing 39 located thereabove. With an adjusting nut 98 that can be screwed on to an end thread on the bearing bolt 95 and which e.g. by means of a sleeve 97 is effective against the preferably flattened upper side of the articular housing 39, the bearing part 53 can be tightened in its respective rotational position and released again. To facilitate manual rotation, gripping grooves 99 or gripping ribs are provided on the front side of the bearing part 53. By means of a scale in the region of the joint between the articular housing 39 and a part, e.g. the sleeve 97 that can rotate with the bearing part 53, the desired rotational setting of one or both bearing parts 53 can be adjusted accurately.

The third degree of freedom of the bearing part 53 is provided in that it is settable in the longitudinal direction of the swivel axis 5 and can be fixed in the respective set position. This is made possible by a lateral adjusting guide 101 effective in the transverse direction Y which is integrated in the bearing of the bearing bolt 95 in the articular housing 39. A longitudinal hole 96a is to be provided for this purpose. It is advantageous to associate a transmission 102 with the lateral adjusting guide 101 which, in the present exemplary embodiment, is formed by an eccentric transmission. By actuating an associated drive element, here an eccentric bearing ring 103, its rotary movement is converted into a lateral movement for the bearing part 53 directed along the swivel axis 5. The eccentric bearing ring 103 has a vertical bearing bore 104 with which it is rotatably mounted with little play on the bearing bolt 95. The eccentric bearing ring 103 has on one side a hub part 105 that is eccentric of the bearing bore 104 with which hub part it is rotatably mounted with little play in the vertical bearing bore 106 of a compensating ring 107 which fulfils the purpose of compensating components of movement of the eccentric drive that are directed transverse to the swivel axis 5. For this purpose the compensating ring 107 is provided on either side with two vertical guide surfaces 108 extending at right angles to the swivel axis 5 which are formed by the external flats of the compensating ring 107 and can be displaced on two corresponding guide surfaces 109 of a longitudinal guide that is transverse to the swivel axis 5 and in this way are also secured against rotation. The guide surfaces 109 are the mutually facing surfaces of an—when viewed from above—approximately rectangular recess 111 in the associated articular housing 39 on the horizontal recess base 112 of which the eccentric hub part 105 and the compensating ring 107 slide. The guiding wall 96 of the articular housing 39 tapered by the recess 111 forms on its underside a horizontal guide surface 114 for the associated bearing part 53. In the lateral adjusting guides 101 the associated bearing part 53 can be adjusted continuously and set and fixed in a range of adjustment from 0 to about 2 mm, which purpose is served by the adjusting nut 98. The range of adjustment is directed inwards from an associated normal position. By this means a so-called initial bend in the starting region of the associated Bennett movement can be set for each bearing 11. For this purpose the eccentric bearing ring 103 has a protrusion preferably formed as a flange 103a that bears on the compensating ring 107 and/or on the upper side of the associated articular housing 39 and which preferably has gripping grooves or a knurl on its outer periphery which facilitate manual gripping to rotate the eccentric bearing ring 103. By means of a scale in the joint region, preferably between the flange 103a and the articular housing 39, the respective setting can be judged and indicated. The flange 103a preferably has a snap-in pin that can be bent out vertically and which can elastically snap into snap-in depressions in the upper side of the compensating ring 107 or in the articular housing 39 and thus forms an arrest for stepwise adjustments.

With each joint 11 a further, fourth degree of freedom is associated with the bearing part 53 for the optional adjustment of the shift angle 52. Since in the present embodiment the lateral guide surface 49 on the rear side is part of a component that is separate from the associated bearing part 53, namely the lateral guide part 54, the shift angle 52 of the lateral guide surface 49 can be adjusted stepwise or continuously independently of the other guide surfaces of the associated bearing part 53 by exchanging or adjusting the lateral guide part 54. This purpose is served by different lateral guide surfaces 49 having different shift angles 52 which can be arranged on one or more exchangeable lateral guide parts. FIGS. 12 to 14 show a lateral guide part 54a on which a plurality of different lateral guide surfaces 49a to 49e are arranged offset from one another in the circumferential direction. One of these lateral guiding surfaces, namely the lateral guide surface 49a is arranged parallel to the longitudinal axis of the lateral guide part 54a and also to the swivel axis 5, and it therefore replaces the cylindrical outer surface 55 of the cylindrical lateral guide part 54 shown in FIG. 6.

Figure 16:
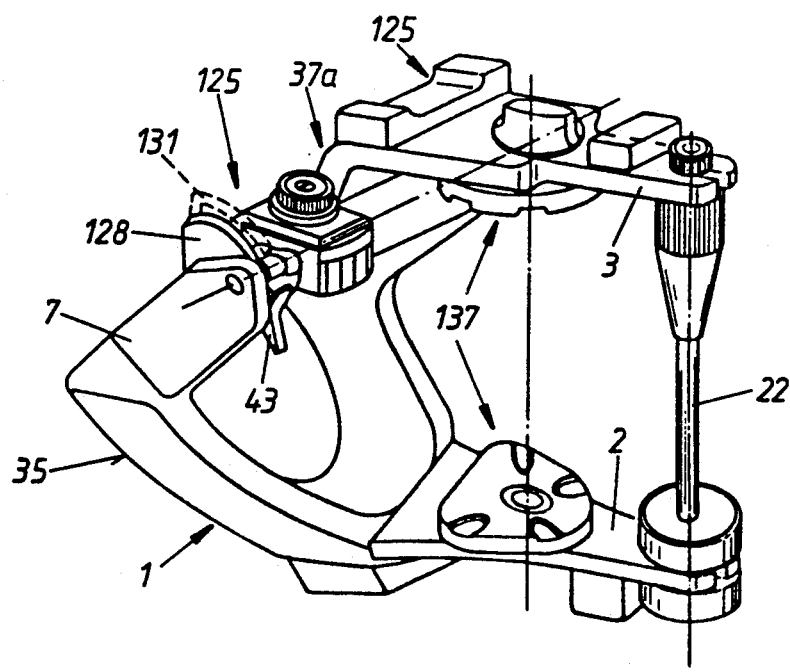
FIG. 16 shows the left joint region of an articulator according to the invention in a modified embodiment in a perspective representation.

With the lateral guide part 54a, shown in FIGS. 14 to 16, the lateral guide surfaces 49a to 49e are arranged on the head part 116 of a bolt shaft 117. In the present exemplary embodiment five shift angles 52 are realised that are gradated relative to one another and which extend over a range of about $-10°$ to $15°$ for the shift angle of the lateral guide surface 49e, up to about $+30°$ to $35°$ for the shift angle of the lateral guide surface 49c. The lateral guide surface 49a is formed axis-parallel in the Y direction so that its shift angle is equal to zero. The lateral guide surface 49e with the shift angle 52 lying in the negative region can be realised by a segmental radial projection 116a in the lateral outer end region of the head part 116.

The cylindrical bolt shaft 117 has a thread 118 on its free end and can be inserted from the outside with the bolt shaft 117 into a bearing bore of the associated articular housing 39 and mounted therein with little play. The bearing bore is arranged so that relative to the swivel axis 5 it is offset so far to the rear and a few mm lower that the lateral guide surfaces 49a to 49e can be pivoted into a position corresponding to the contact point C by rotating this lateral guide part 54a. To hold the bolt shaft 117 a threaded nut 119 (FIG. 4 and 5) that can be screwed onto the bolt shaft 117 is provided with a knurl on its periphery which sits in an uppersided slit recess 120 in the associated articular housing 39 that is open to the rear and is dimensioned so that its periphery, by which it can be grasped, projects slightly from the outer surface of the articular housing 39. For adjustment purposes the lateral guide part 54a is grasped at the head part 116 and after undoing the threaded nut 119 is turned so that in the O-position of the joint 11 the associated lateral guide surface 49 bears against the spherical head 36a in the centre position of the upper part 37a.

It is also possible within the scope of the invention to use a lateral guide part 54b shown in FIG. 15 that is comparable to that described above, of which the head part 116 has on its outer surface a plurality of lateral guide surfaces 49a to 49e that differ from one another with regard to the shift angle 52, and which merge into one another smoothly in the peripheral direction in the form of an envelope curve surface. Continuous adjustment of the shift angle 52 is hereby made possible. Furthermore the lateral guide part 54b and also the lateral guide part 54 shown in FIG. 6 can be formed like the lateral guide part 54a and can be tensioned and released accordingly.

A protrusion guide 125 or longitudinal guide shown in FIG. 16 is preferably associated with the joints 11 which makes it possible to displace the upper part 37a in the joints 11 parallel to the vertical longitudinal centre plane E1. For this purpose an upperside and underside guide part is associated with each joint 11 which are displaceable in the longitudinal direction of the articulator 1 alongside one another. In the present embodiment a guiding groove 127 preferably formed by a peripheral groove in the associated articular head shaft 36b is provided on each side in which a ledge or disc-like guiding slide 128 engages and during the protrusive movement is guided therein. The upper part 37 is hereby guided longitudinally although the Bennett guide surfaces 47 release the spherical heads 36a.

The guiding slide 128 is preferably designed so that it forms a transmission drive part for a forward protrusion movement of the upper part. The guiding slide 128 is a rotary part that is arranged behind the associated articular head 36 and with regard to an axis of rotation is formed in the sense of an upward inclination or eccentrically. The rotary-disc-form guiding slide 128 can be attached to the lateral guide part 54 and be made of one or two parts. For this purpose the guiding slide 128 can have a bolt shaft 117, as is indicated in FIG. 18, with which it can be mounted as a part exchangeable for a lateral guide part 54, 54a, 54b. Owing to the upward inclination, with uniform rotation of both guiding slides 128 forwards or clockwise, the upper part 37a is moved forwards due to the eccentric inclination surface 129, and the guiding slides 128 driven by the eccentric fulfill the function. The inclination of the guiding slides 128 is preferably dimensioned so that when they are rotated a protrusive movement of several mm, e.g. up to 5 or even up to about 10 mm can be effected. For backward movement of the upper part 37a the guiding slides 128 must be turned in reverse. The upper part 37a can be returned automatically by the resilient elastic return force of the locking bow 43 or its resilient part 73 and the existing eccentric transmission can control the return movement deliberately.

Figure 17:
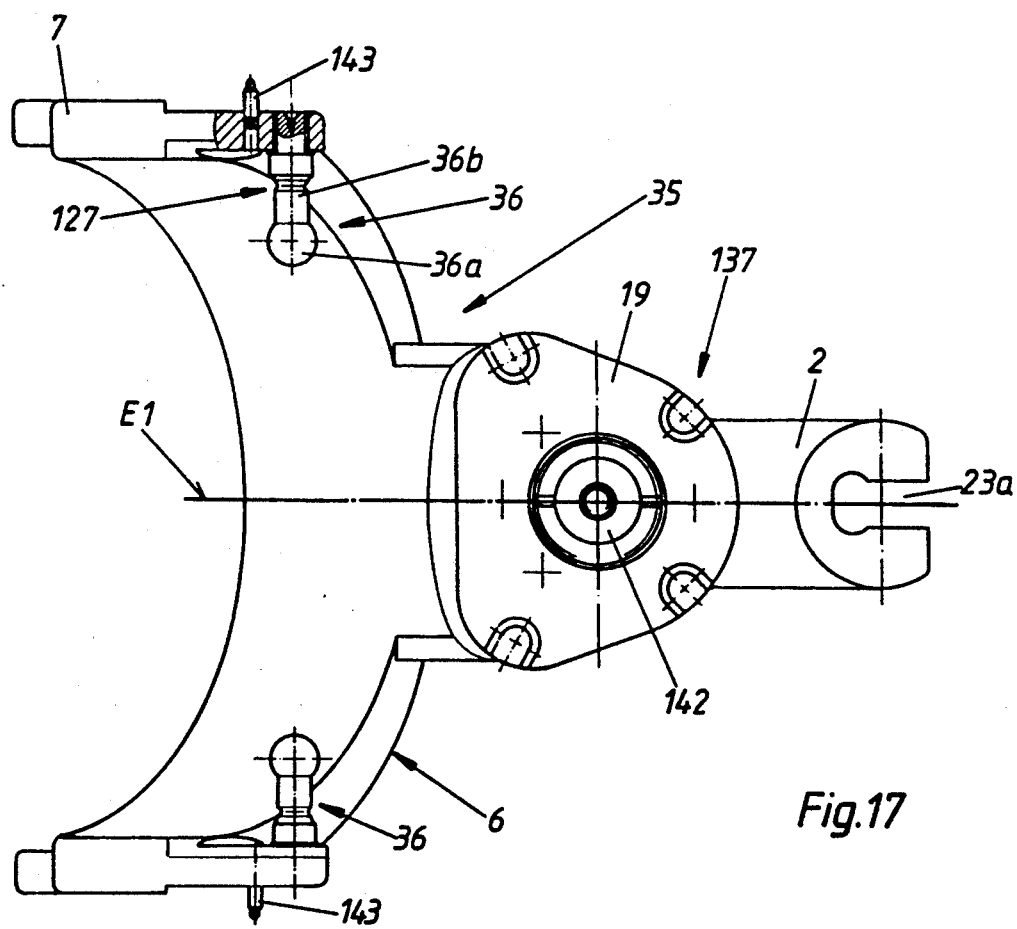
FIG. 17 shows the lower part of the articulator in plan view.
Figure 20:
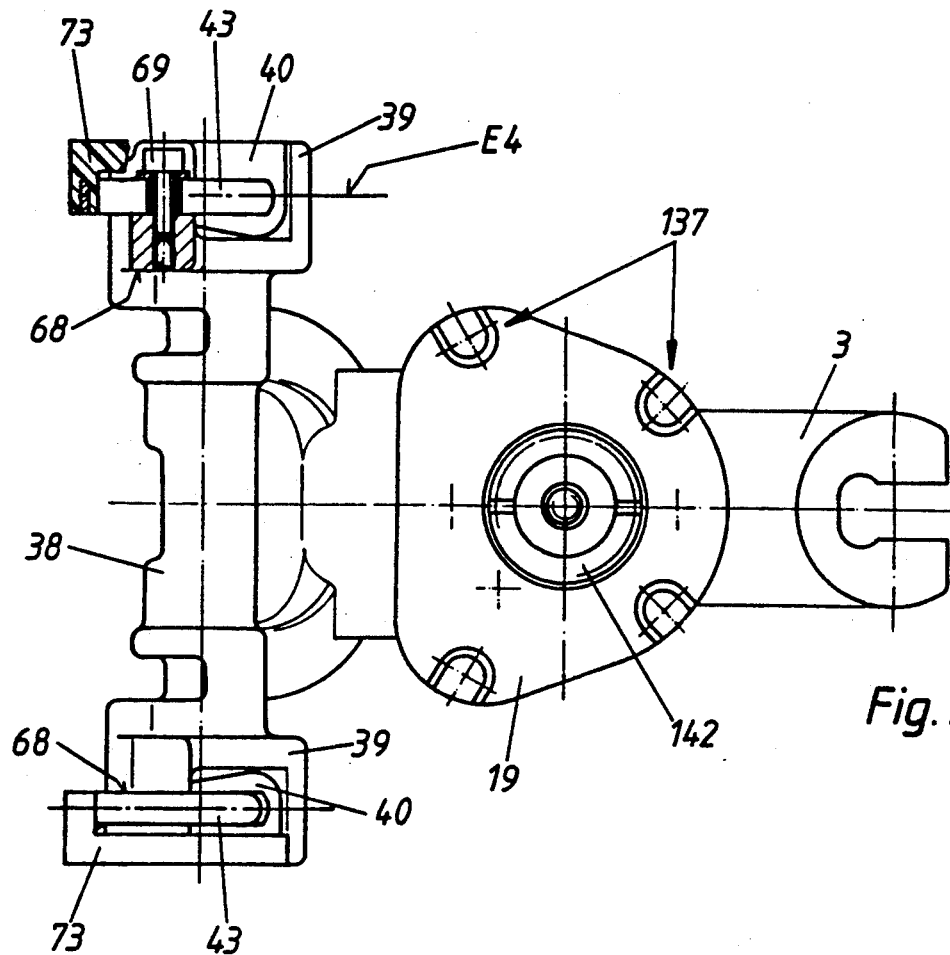
FIG. 20 shows a second upper part of the articulator in side elevation from the left.
Figure 21:
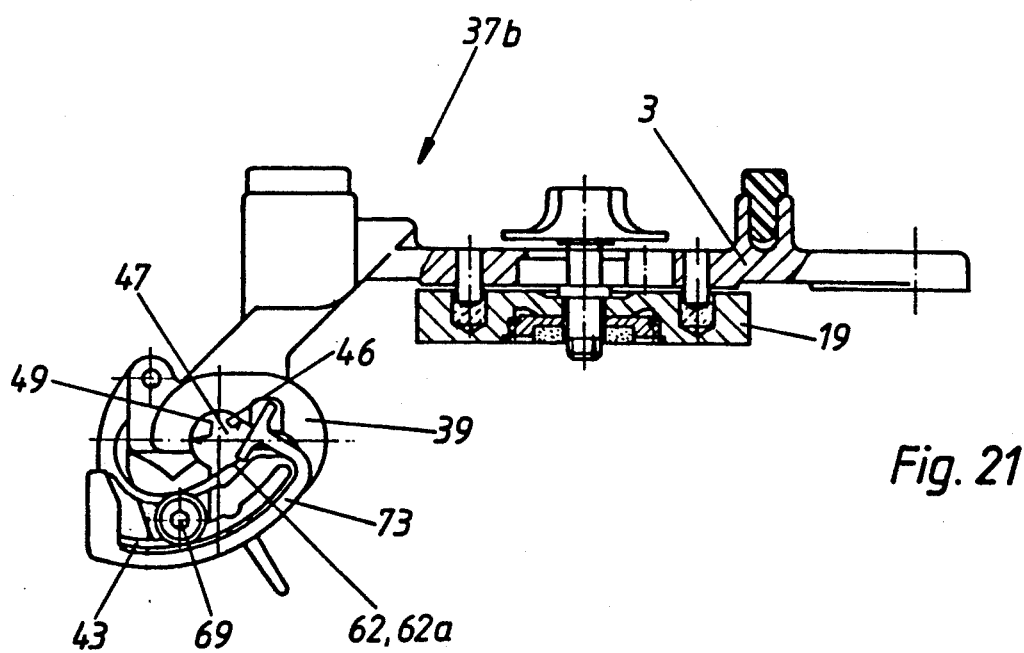
FIG. 21 shows the second upper part in lower elevation.

Within the scope of the invention it is possible to provide the guiding slides 128 with respective hook-shaped guide parts 131, indicated in outline in FIG. 17, which with the inclination surface 129 forms a guiding groove whereby compulsory guidance for the movement backwards is also created.

Provided on the semi-circular-shaped disc periphery of the guiding slide 128, shown clearly in particular in FIG. 19, is a scale which enables an indication or reading in mm, starting from the O-position, for the protrusion region 129a of the inclination surface and the retrusion region 129b. Between these two regions a rounded recess 133 is provided on the periphery of the existing disc shape which represents an interruption in the protrusion guiding 125. When the protrusion guide 125 is in the inoperative position the guiding slides 128 with their recesses 133 are each located in the region of the associated articular head shaft 36b. In this O-position the upper part 37a can effect laterotrusive movements because the guiding edges 128a of the guiding slide 128 are not engaged with the associated guide grooves 127. From the recess 133, which represents a U-position, the guiding edge 128a of the protrusion region 129a has a positive inclination while the guiding edge 128b of the retrusion region 129b has a negative inclination, i.e. it descends. Both guide edges have a convex curve shape.

Formed on the inside of the disc-shaped guiding slides 128 is a head piece 135 that has an outer surface section 136 in the middle region of the recess 133 that forms a cylindrical-section-shaped lateral guide surface 49 for laterotrusive movements and can be formed axis-parallel or inclined in the sense of a desired shift angle 52. On both sides next to this outer surface section 136 the head part 135 is tapered in cross-section in the sense of a recess 137 whereby an axial extension 138 carrying the outer surface section 136 is formed.

The two existing guide grooves 127 and the guiding edges 128a, 128b of the guiding slides 128 are formed so that in cross-section they diverge or converge, in particular in the shape of a wedge, to facilitate leading of the edge regions into the guide grooves 127. For this purpose the edge regions of the guiding slides 128 and the guiding grooves 127 have oblique flanks that match one another.

Because of its adjustability the above-described adjustable articulator 1 can be used for work which has to meet exacting requirements, because the upper jaw movements possible with the articulator come very close to the anatomical relationships of the human body. However, there is also dental technical work for which an adjustable articulator 1 of this kind is not necessary and which can also be carried out by so-called mean value articulators with which adjustment of the aforementioned degrees of freedom is not possible.

The articulator 1 described above preferably has a second upper part 37b associated therewith with which the afore-mentioned degrees of freedom cannot be adjusted as desired but are set permanently in the sense of a predetermined mean value. The second upper part 37b can be exchanged as desired for the first upper part 37a, which can be done simply and quickly due to the above-described user-friendly centric locks 42. The articulator 1 can thus be equipped as desired as an adjustable articulator or as a so-called mean value articulator.

In the second upper part 37b the guide surfaces of the guide recesses 40, namely the sagittal guide surfaces 46, the Bennett guide surfaces 47 and the lateral guide surfaces 49 are unchangeably formed on the associated articular housing. The rear sided sections of the articular housing 39, which have the lateral guide surfaces 49, are formed in one piece, whereby integral housing blocks result. In other respects the second upper part 37b is the same as the first upper part 37a, i.e. it also has the afore-mentioned locking bows 43 which in each case form a respective fixed and movable bearing on the same side for more accurate centering of the upper part 37b on the lower part 35. Despite the exchangeability of the upper parts, this embodiment enables great precision and accurate work, as there is a common reference or centering plane E4 for both upper parts 37a, 37b and the common lower part 35.

Furthermore both upper parts 37a, 37b and the lower part 35 have a further feature which will be explained with reference to the following embodiment.

During manufacture of a lower jaw- and/or upper jaw tooth model OK, UK it is in many cases necessary to remove the tooth model from the articulator 1 at intervals in order to, e.g. measure it in a particular manner, and to remount it onto the articulator 1. To make this possible it is known to provide a form-locking effective centering device 137 between the primary base 19 and the associated tooth model UK, OK which with reliable abutment of the tooth model against the associated primary base 19 prevents horizontal relative displacement of the tooth model UK, OK. Such a centering device can very advantageously be formed by elevations and depressions having preferably oblique flanks which engage one another in a form-locking manner and with fitting precision. In the present embodiment a plurality of, e.g. four, recesses 138 are provided and arranged in the edge region of the facing surfaces of the tooth model UK or OK and the associated primary base 19, into which recesses, correspondingly formed projections 139, e.g. formed by means of a corresponding model base former (not shown) of plaster of paris, engage with fitting precision. The side faces 141 of the recesses 138 and projections 139 on the tooth model are formed by oblique, locating surfaces adjoining one another so that it is possible to join with one another the two fitting parts in an easy, user-friendly manner. To hold them together detachably a magnet device is provided having a permanent magnet on one part, preferably in the primary base 19 and a holding part on the other part, preferably on the tooth model, cooperating with the permanent magnet. In the present embodiment in FIGS. 3, 5, 17, 20 and 21 a permanent magnet 142 is embedded into the primary socket 19. It is preferably a magnet disc that is screwed into the primary base part by means of threads, and preferably an extended fastening screw 15 can be provided for the tooth model UK or OK that passes through the associated articulator arm 2, 3, the primary base 19 and the permanent magnet disc 142 in holes.

In the present embodiment the primary bases 19 or the centering devices 137 are fixed exactly, here by means of alignment pins 16 and associated alignment holes 17, on the associated articulator arm 2, 3 with reference to the reference plane E4 or the fixed bearing 42a. Furthermore the primary bases 19 or the centering devices 137 are arranged in precise relation to a reference plane extending in or parallel to the vertical plane E3 and are aligned in fitting precision. The accurate arrangement relative to the vertical reference plane E4 can be served by, e.g. the locking bow 43 belonging to the bearing surface 68 arranged vertically and longitudinally on the fixed bearing side A device (not shown) can serve to arrange the primary base 19 with fitting precision.

This accurate arrangement of the fitting surfaces of the locking device 137 relative to the reference planes makes exchange of the upper parts 37a, 37b as desired possible, with the fitting accuracy of the fitting points for the tooth base UK and OK ensured.

Furthermore this embodiment enables so-called cross-over mounting, i.e. a tooth base UK or OK can also be installed in a second articulator 1 designed according to the invention in the manner described above. This has the advantage that the articulator 1 does not need to be sent together with the associated tooth model in order to make accurate arrangement of the lower jaw- and/or upper jawtooth model UK, OK possible.

Indicated by 143 in the tragus medialis are prongs 143 projecting laterally from the frame limbs 7 for a facial arc (not shown).

What is claimed is:

1. A dental articulator including two articulator arms which extend forwardly in the working positions thereof, one said arm being mounted in two swivel and sliding joints for pivotal motion about a swivel axis extending at right angles to a vertical longitudinal center plane of said articulator, said joints being arranged on opposite sides of the vertical longitudinal center plane as mirror-images, each said joint being formed by an articular recess in an articular housing; an a spherical head engaging through an opening in the articular recess; said articular recess having a sagittal guide surface, a Bennett guide surface and a lateral guide surface; each said swivel and sliding joint having a locking device with a locking element operatively associated therewith for locking an associated swivel and sliding joint in an O-position defining a final biting position, said locking element being adjustable between a locking position and a releasing position facilitating sliding movement in the associated swivel and sliding joint; a resilient part being associated with the locking element, said resilient part consisting of a resiliently elastic material extending beyond the locking element and resiliently contacting the joint part in the releasing position of the locking element and being subjected to a pretensile force urging the joint into the O-position.

2. An articulator as claimed in claim 1, wherein in the locking position the locking element urges the associated joint into said O-position and pushes elastically against the spherical head with a force that is directed towards the rear, obliquely upwardly and at right angles to the swivel axis of said swivel and sliding joints.

3. An articulator as claimed in claim 1, wherein a resilient part is operatively connected between the lower part and the upper part so as to in the releasing position of the locking element urge each swivel and sliding joint into its O-position and hold the sagittal guide surface and the spherical head in sliding contact.

4. An articulator as claimed in claim 3, wherein the resilient part is integrated with the locking element in a laterally outward position offset adjacent an associated articular housing.

5. An articulator as claimed in claim 1, wherein the locking element is adjustable beyond the releasing position into an open position for vacating the opening of the articular recess.

6. An articulator as claimed in claim 5, wherein clamping and elastic latching means detachably fasten the locking element in the locking position, in the releasing position and in the opening position.

7. An articulator as claimed in claim 1, wherein the spherical articulator heads are arranged coaxially with the swivel axis and extend towards one another such that in locking positions thereof the locking elements engage below the spherical heads.

8. An articulator as claimed in claim 1, wherein the locking element consists of a resilient material and is subjected to elastic pre-stressing to generate a bending stress towards an associated spherical head.

9. An articulator as claimed in claim 1, wherein the locking element has in the region which in the locking position cooperates with the spherical head, a divergent wedge-shaped recess forming a fixing groove extending in the direction of movement into which the spherical head engages.

10. An articulator as claimed in claim 1, wherein the articular recess has a concave rounding between the sagittal guide surface and the Bennett guide surface which has a radius larger than the radius of the spherical head.

11. An articulator as claimed in claim 1, wherein the spherical head is fixed as a three-point bearing in the articular recess when the associated swivel and sliding joint is in the O-position, whereby one bearing point bears against the sagittal guide surface in the vertical plane containing the swivel axis, a second bearing point lies against the lateral guide surface and a third bearing point lies against the locking element in the locking position thereof.

12. An articulator as claimed in claim 1, wherein the articular housing is pivotable about the swivel axis and fixed in the assumed adjusted tilting position.

13. An articular as claimed in claim 1, wherein the articular recesses are each formed in an articular part which is pivotable about a vertical swivel axis and fixed in the respective tilting position, and the vertical swivel axis intersects a horizontal swivel axis.

14. An articulator as claimed in claim 13, wherein the articular recesses are each formed in a bearing part which is displaceable in a guide extending in the longitudinal direction of the horizontal swivel axis and is fastenable in the assumed adjusted displacement position.

15. A dental articulator including two articulator arms which extend forwardly in the working positions thereof, one said arm being mounted in two swivel and sliding joints for pivotal motion about a swivel axis extending at right angles to a vertical longitudinal center plane of said articulator, said joints being arranged on opposite sides of the vertical longitudinal center plane as mirror-images, each said joint being each formed by an articular recess in an articular housing and a joint part extending through an opening in the articular recess, said articular recess having sagittal guide surface and a rear limiting surface, each said swivel and sliding joint being operatively associated with a locking device having a locking element for locking the therewith associated joint part in an O-position comprising a final biting position in the articular housing, said locking element being a crescent-shaped swivel part having a first limb including a rear portion which is mounted on the articulator arm comprising the articular housing for pivotable motion between a locking position and a releasing position extending in parallel with the longitudinal center plane; means for arresting said limb in a locking position; a second limb consisting of a resiliently elastic material extending in a swiveling plane at right angles to the first limb and in the locking position thereof resiliently engaging from below an associated joint part; means subjecting the second limb in the locking position to an elastic pretensile force extending in direction of the joint part, and the second limb in the released position thereof being at a distance from the swivel axis of the swivel part which is shorter than the distance between the swivel axis and the surface of the joint part which is gripped from below by the second limb.

16. An articular as claimed in claim 15, wherein the locking element has the crescent-shaped swivel part in the locking position thereof engaging with a free end region behind a therewith associated spherical articular head.

17. An articular as claimed in claim 16, wherein the crescent-shaped swivel part is mounted pivotably rearwardly of the swivel axis in a position with a free end thereof pointing forwardly and from a rearwardly tilted open position is pivotable into a forwardly tilted locking position.

18. An articulator as claimed in claim 15, wherein the locking element has a securing extension extending beyond a locking section which is angled relative to the locking section so as to block the opening of the articular housing when the locking element is in the releasing position.

* * * * *